United States Patent [19]
Yoon

[11] Patent Number: 4,794,927
[45] Date of Patent: Jan. 3, 1989

[54] ELASTIC LIGATING RING CLIP

[76] Inventor: Inbae Yoon, 2213 Forest Ridge Rd., Timonium, Md. 21093

[21] Appl. No.: 789,663

[22] Filed: Oct. 21, 1985

Related U.S. Application Data

[62] Division of Ser. No. 370,170, Apr. 20, 1982, Pat. No. 4,548,201.

[51] Int. Cl.$^4$ .............................................. A61B 17/12
[52] U.S. Cl. .................... 128/326; 128/325; 128/346; 128/303 A; 128/327
[58] Field of Search ............... 128/303 A, 326, 325, 128/346, 327; 29/235; 24/236–239, 115 H, 30.5 R, 129 R, 481, 482; 206/805, 159, 339, 343, 345, 346, 347; 251/9, 10

[56] References Cited

U.S. PATENT DOCUMENTS

| | | | |
|---|---|---|---|
| 3,726,279 | 4/1973 | Barefoot | 128/327 |
| 3,866,611 | 2/1975 | Baumrucker | 128/346 |
| 3,924,738 | 12/1975 | Poupitch | 206/805 |
| 4,200,107 | 4/1980 | Reid | 128/346 X |
| 4,312,487 | 1/1982 | Kimura | 206/805 |
| 4,485,814 | 12/1984 | Yoon | 128/327 |

FOREIGN PATENT DOCUMENTS

| | | | |
|---|---|---|---|
| 1534916 | 6/1967 | France | 128/346 |
| 0556424 | 10/1943 | United Kingdom . | |

Primary Examiner—Richard J. Apley
Assistant Examiner—Paul Prett
Attorney, Agent, or Firm—Robert E. Bushnell

[57] ABSTRACT

Disclosed is band 10', shown in a relaxed condition, made of a segmented, solid ring 12 of an elastic material. The segmented ring 12 has a disc or cylindrical shape and contains a pair of parallel lumena 14, 15 extending between opposite bases 13. A clip action is provided by outer sections a and c of solid ring 12 coaxially disposed on either base 82a, 82b, respectively, of ring b. Sections a and c are flexibly hinged to ring b by solid intermediate sectors 84a, 84b. Preferably, sections a, c, ring b, and sectors 84a, 84b are all integral volumes of the same piece of segmented elastic material. In effect, each of sections a, c and ring b contain a pair of parallel lumena 14a, 15a, 14c, 15c, 14b, 15b, respectively with each pair of lumena diametrically aligned with sectors 84a, 84 b.

27 Claims, 6 Drawing Sheets

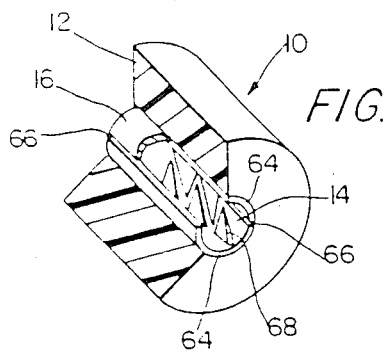
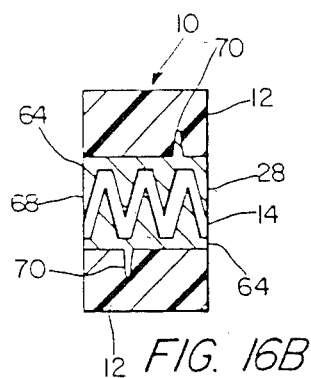
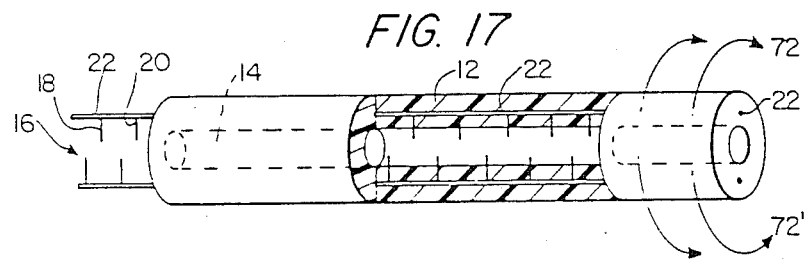
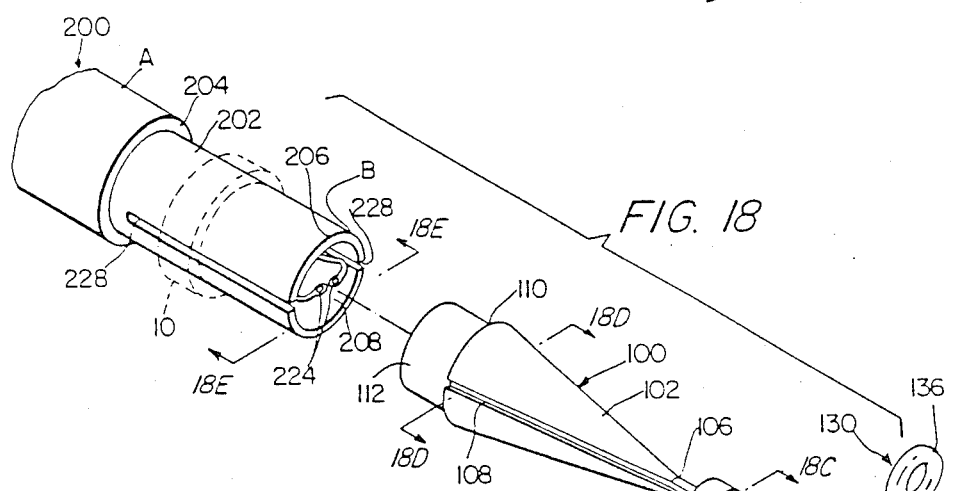
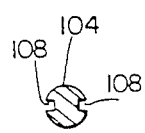
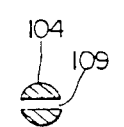
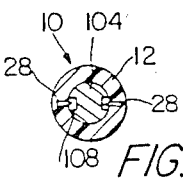
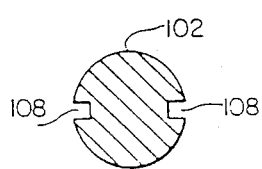
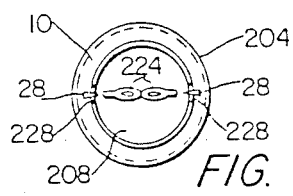

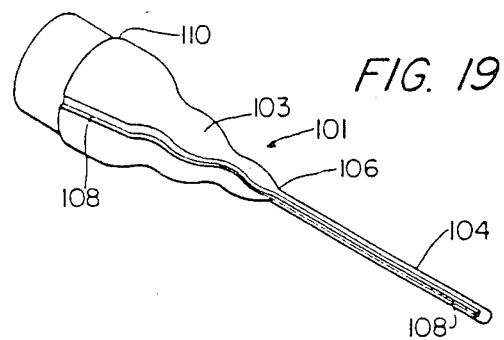
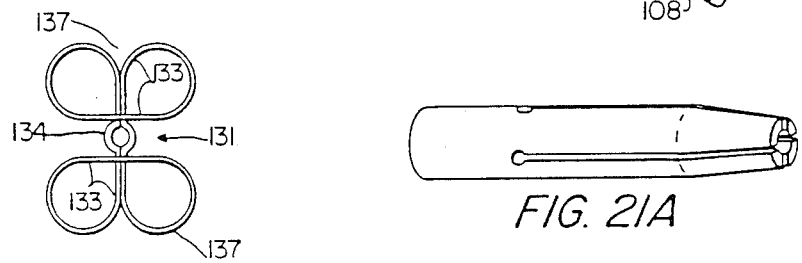
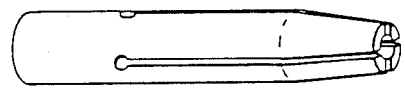
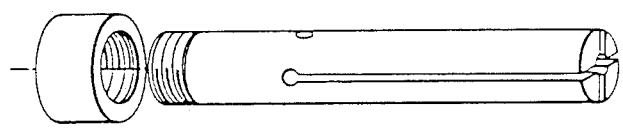
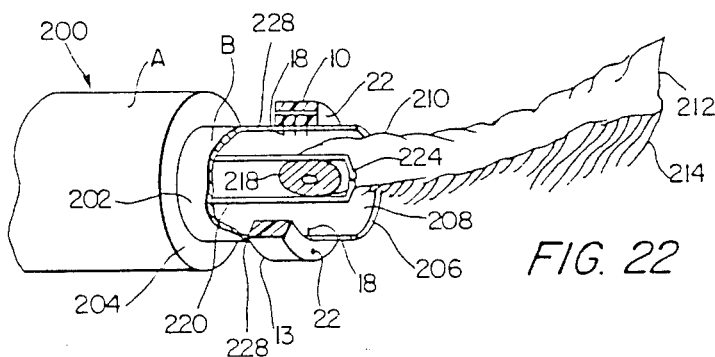
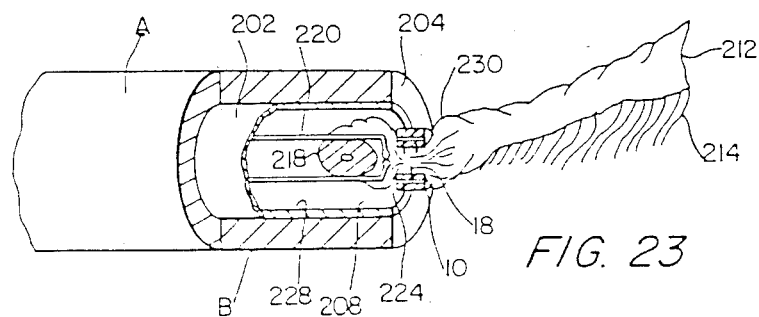

ELASTIC LIGATING RING CLIP

CROSS REFERENCE TO RELATED APPLICATIONS

This is a division of application Ser. No. 370,170 filed Apr. 20, 1982 now U.S. Pat. No. 4,548,201.

TECHNICAL FIELD

The present invention pertains to a surgical method for ligating anatomical organ structures and to the instruments and devices used therein and, more particularly, to an endoscopic method and the devices and applicators used to surgically apply an elastic band around a loop of a linear organ structure.

BACKGROUND ART

Occasionally in the surgical practice of human and veterinary medicine, it is desirable to impair or halt the fuction performed by a bodily tissue member such as a linear ligament or tubular organ. Typically, this is done by severing, ligating, shortening or occluding the structure of the bodily member. In one of the more common methods, electrocoagulation, an instrument is inserted into the body cavity through a small incision and heat is applied to the organ, in situ, until the tissue burns and is severed or, if a tubular organ, its passageway occluded. Obstruction of a surgeon's view by the smallness of the incision and the proximity of other bodily members however, creates a risk that a member other than the one intended will be inadvertently injured by cauterization or perforated by the instrument, perhaps without the surgeon's awareness.

Another method, occasionally used to occlude elongated tubular organ structures, relies upon a small, three-piece clip. A small incision is made in the wall of the body cavity and an applicator holding the clip in its distal end is inserted into the cavity. The applicator is manipulated to apply the clip across the tubular organ in situ. A small bias spring slips over the ends of the arms of the clip to lick the clip into a closed position so that sharp teeth on the opposite ends of the arms penetrates and firmly grasp the tubular structure. The locking action of the spring causes the arms to compress and occlude a cross-section of the tubular structure. The necessary rigidity of the arms of a clip of this type means that the size of a clip must be carefully tailored to the dimensions of the tubular structure. If too small, a clip will fail to completely engage the structure, and will, therefore, cause only a partial occlusion. If too large, the clip will present a hazard to neighboring organs. Furthermore, if a clip is applied obliquely to the length of the tubular structure, it will likely fail to cause a complete occlusion and thus render the operation a failure unless the oblique application is immediately discovered. If discovered, however, an obliquely applied clip cannot be easily removed due to the locking action of its bias spring. Consequently, the applicator must be removed through the incision, loaded with a second clip, and re-inserted to correctly apply the second clip to the tubular structure. Occasionally, it may be necessary to repeat these steps several times before one clip is successfully applied so as to completely occlude the passageway inside the tubular structure. Another difficulty arises from the propensity of these small clips to fall out of the applicator before its bias spring fully is engaged, thus permitting the clip to freely tumble about within the body cavity. Unless promptly located and retrieved, the sharp teeth of the open clip will likely injure and possibly, penetrate, an unintended organ or structure.

The Pomeroy technique, another common method, is an open laparotomy procedure often used for tubular ligation that requires a larger incision to be made in the wall of a body cavity. The bodily tissue member to be operated upon is manually pulled out of the cavity through the incision and drawn into a loop or band, forming a knuckle. The loop is ligated by tying it without catgut. If the loop is part of an elongated tissue organ, the tightness of the catgut ligature occludes the passageway inside the tubular structure. The knuckle, that is, the proximal end of the loop is then cut off and taken to a pathological laboratory for identification. The large size of the required incision and concomitant inconvenience of the patient, a long hospital stay, a high incidence of infection, and an unnecessarily large scar are particular disadvantages of this method.

Although the pomeroy technique is the most accepted and popular method, the introduction of the endoscope into general surgery and the field of gynecology permits a Pomeroy-like technique to be utilized through an endoscope (laprascope) ring applicator. In this Pomeroy-like technique, a much smaller incision is made in the body cavity wall to permit insertion of a multi-cylinder laparoscopic applicator bearing a small elastic ring stretched over its distal end. Forceps extending out of an operating channel inside the applicator completely grasp a cross-section of a linear organ structure such as a Fallopian tube or round ligament. When retracted, the forceps draw the linear organ structure into a loop with the knuckle of the loop pulled into the operating channel of the applicator. Further manipulation of the applicator causes relative movement of two applicator cylinders, ultimately forcing the elastic ring over the mid-section of the loop, thereby completely and automatically occluding the tubular structure. The loop is then released and the applicator withdrawn. Although this method is comparatively quick, simple and reliable, if the loop is not of sufficient size, it is possible for the ring to slip over the knuckle, thereby releasing the loop from occlusion. This may also happen even with a loop of adequate size, if the occluded bodily member is subsequently subjected to vigorous physical motion (e.g. pelvic examination) before fibrosis of the ring occurs.

In all of the presently used methods for severing, ligating or occluding the structure of a bodily tissue member, it is quite possible to inadvertently operate upon the wrong organ or structure. This is particularly likely in a method where the surgeon's field of view is either limited by the minuteness of the incision or constructed to the image provided by an endoscope. For example, in a laparoscopic tubal sterilization of a human female, it is possible to mistakenly grasp and occlude either the round ligament or the ovarian ligament, or even a bowel structure rather than a Fallopian tube. Discovery of inadvertent occlusion of the wrong structure may be delayed by a period of days or longer, until the patient's discomfort or bodily malfunction necessitates further surgery.

An additional disadvantage of presently used methods lies in the frequency with which the bodily member to be operated upon is unusually oversize, either due to natural causes or to infection. Unless its size is detected during surgery, any attempt to ligate or occlude the member via a small incision technique will likely fail due to either the inadequate size of the occluding device or the smallness of the operating channel of the applicator.

STATEMENT OF INVENTION

Accordingly, it is an object of the present invention to provide a safer method for surgically ligating linear organ structure.

It is another object to provide a simple method for surgically ligating a linear organ structure.

It is yet another object to provide a method having a lower failure rate for surgically ligating a linear organ structure.

It is still another object to provide a method suitable for practice by personnel of normal experience for surgically ligating a linear organ structure.

It is still yet another object to provide a method for surgically applying a ring clip to a linear organ structure.

It is another object to provide a ring clip for surgically ligating a linear organ structure.

It is a further object to provide an occluding ring clip for retentively engaging a bodily tissue member.

It is a yet further object to provide a ring clip for retentively holding a bodily tissue member in a ligated formation.

It is a still further object to provide a ring clip for retentively engaging a membrane adjoining an occluded or shortened linear organ while holding the linear organ in an occluded formation.

It is another object to provide a method and kit for preparing an applicator to surgically ligate a linear organ structure.

It is an additional object to privide a method and sterile and disposible kit for preparing an applicator to surgically ligate a linear organ structure.

It is a still additional object to provide a method and kit for preparing an elastic ring or ring clip applicator to surgically ligate a linear organ structure.

It is a yet additionally object to provide a method and kit for uniformily distributing the force applied to an elastic ring or ring clip while loading the ring unto an applicator.

These and other objects are achieved in a Pomeroy-like surgical method in which a ring clip formed by a non-tissue reactive, elastic band having a lumen obstructed by a partially embedded, protruding clip when the band is in a nearly relaxed condition, is applied across adjacent sectional lengths of a bodily tissue member drawn into a loop formation. The clip of the elastic band may have one or more elements (e.g., needles, pins or teeth) protruding into or about one of the lumen in one or more files, thus necessitating preferential orientation of the band during loading onto an applicator. Preferential orientation may be used to assure placement of the protruding clip elements with respect to the adjacent sectional lengths. When radially aligned with the tips on the tongs of applicator forceps, the clip elements come to rest harmlessly between the adjacent sectional lengths, thereby obstructing the lumen and preventing the band from slipping over the neck of the loop. Additionally, the elastic force applied by the band to the clip elements causes the elements to retentively grasp and penetrate any tissue membrane between the adjacent sectional lengths, thereby preventing the band from slipping along the length of the loop and over its neck.

The ring clip can be supplied in multiple members in a disposible, sterile kit with a flexible ring dilator and ring clip loader. The dilator is used to uniformily distribute finger pressure force to one side of the ring clip as the ring clip is stretched across a conic ring loader adapted to receive the retentive members and onto a similarly adapted distal end of a ring clip applicator.

When loaded with one or more ring clips, the ring dilator and ring clip loader are removed from the applicator and the applicator is inserted into the body cavity through a small incision in the cavity wall. Forceps extending from the operating channel of the applicator grasp the bodily tissue member and thereby forming a loop as the knuckle is drawn into the operating channel. Relative movement of two cylindrical parts of the applicator discharges the ring clip over the knuckle and across the loop of the tissue member. The forceps then release their grasp of the occluded tissue member and the applicator is withdrawn from the body cavity. The applicator may be used to apply a ring clip with or without an endoscope.

BRIEF DESCRIPTION OF DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein:

FIGS. 16A and 16B are a partially cut-away orthogonal view and a sectional front view, respectively, of another embodiment.

FIG. 17 is a partially cut-away isometric view shwoing one method for making an embodiment of the type shown in FIG. 8.

FIG. 18 is an exploded orthogonal view showing a kit and method for using a ring clip.

FIG. 18A is a cross-sectional side view of a ring clip loader.

FIG. 18B is a cross-sectional side view of an alternative embodiment of a ring clip loader.

FIG. 18C is a cross-sectional side view of a cross-sectional side view showing a ring clip around a ring clip loader.

FIG. 18D is a cross-sectional side view of a ring clip loader.

FIG. 18E is a cross-sectional side view showing a phantom ring clip around the distal end of a ring clip applicator.

FIG. 19 is an orthogonal view of an alternative embodiment of a ring clip loader.

FIG. 20 is a front view of an alternative embodiment of a ring clip dilator.

FIGS. 21A and 21B are isometric views of alternative embodiments of a ring clip dilator.

FIG. 22 is a partially cut-away isometric view showing a step in a method for using a ring clip.

FIG. 23 is a partially cut-away isometric view showing another step in a method for using a ring clip.

DETAILED DESCRIPTION OF INVENTION

Typically, a linear organ structure such as a round ligament or a tubular organ (e.g., a Fallopian tube) is attached along its length to a membrane. By way of illustrative example, in the reproductive tubular members of females, both of the Fallopian tubes are formed by three layers: mucosa, muscular layer, and serosa and, except for a short intrauterine portion, are enveloped in the free margin of the broad ligament known as the mesosalpinx. Then, when a small area of a bodily tissue member is grasped with forceps and pulled into the operating channel of a cylinder in the manner described in my U.S. Pat. No. 4,103,680, for instance, those sections of the member adjoining either side of the grasped area tend to fold and form a loop with the grasped area at its apex. Consequently any adjoining mesosalpinx is embraced between the folded sections of the tissue member as the loop is drawn into the operating channel of a ring applicator. Any ligature around the neck of the loop, therefore, concomitantly passes around the mesosalpinx. The Fallopian tube may be described as having four subdivisions. A short, intermediate portion is located inside the uterine wall and leads to the uteral-tubular junction. An isthmic portion connected to the intermediate portion at the junction, is relatively straight and narrow with a thick wall segment. The isthmic portion gradually increases in lumen diameter and shows a diminution in wall thickness as it progresses laterally away from the uteral-tubular junction. An ampullary portion leading from the isthic portion is the longest segment of the Fallopian tube. An infundibular portion is the terminal segment of the Fallopian tube. It is somewhat trumpet-shaped at its ovarian end and is divided into numerous delicate folds as fimbriae which give a fringed appearance. One of these folds is prolonged and is attached to the mesosalpinx. The male vas deferens is also a tubular structure relatively thicker and more rubbery feeling than the Fallopian tubes.

Figure 1:
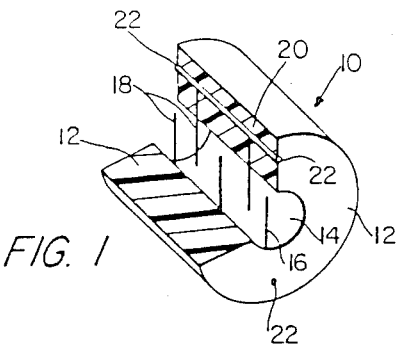
FIG. 1 is an orthogonal projection showing a partial cut-away view of one embodiment made according to the principles of the invention.

Referring now to the drawings, FIG. 1 is a partially cut-away view of a ring-clip band 10 for ligating an anatomical tissue member such as a linear or tubular organ structure.

Referring now to the drawings, FIG. 1 is a partially cut-away view of a ring-clip band 10 for ligating a bodily tissue member such as a linear or tubular organ structure. The band 10, shown in a relaxed condition, is made of a solid ring 12 of an elastic material. The ring 12 has a disc or cylindrical shape and contains a single, centrally positioned lumen 14 extending between opposite bases. A clip 16, preferably made of a less elastic or even a material relatively rigid in comparison to the material of ring 12, has several protruding teeth or needles 18 partially embedded within the ring 12 and extending into the lumen 14 in two diametrically opposed files of axially aligned needles. As shown, each needle 18 has sufficient protruding length to extend more than half-way across the diameter of lumen 14 when ring 12 is in a relaxed condition. Consequently, the two diametrically opposite files form an interleaved or meshed array with alternate needles 18 from opposite files successively obstructing lumen 14 in a single plane that axially bisects ring 12 and lumen 14. The embedded ends 20 of the clip elements 18 are either integral parts of or securely attached to anchor rods 22 completely embedded within and extending between opposite bases of ring 12. Anchor rods 22 are an optional element of the clips 16, serving primarily to facilitate an orderly placement of needles 18 during manufacture of band 10 and to forestall dislocation of needles 18 during stretching and subsequent relaxation of ring 12. When ring 12 is radially stretched to several times its original diameter, lumen 14 is also enlarged. The protruding ends of needles 18 are not subjected to the same stretching force and therefore tend to move radially away from the axis of lumen 14 as ring 12 is stretched, thereby presenting a relatively unobstructed lumen when ring 12 is stretched to several times its original diameter. As ring 12 returns to its relaxed condition, the protruding ends of needles 18 again form an interleaved array and obstruct lumen 14.

Figure 2:
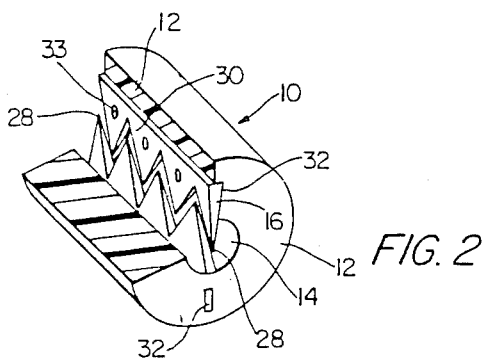
FIG. 2 is an orthogonal projection showing a partial cut-away view of another embodiment.

FIG. 2 shows a partially cut-away view of an alternative embodiment of band 10 made from a solid ring 12 of an elastic material. This ring, also shown in a relaxed condition, has a disc or cylindrical shape with a single, coaxially positioned lumen 14 extending between opposite bases of ring 12. A clip 16 has several protruding serrated elements or teeth 28 partially embedded within the ring 12 and extending into the lumen 14 in two diametrically opposed files of axially aligned teeth. As shown, all of the teeth in each file are joined at their embedded ends and each of the teeth 28 has sufficient protruding length to extending more than half-way across the diameter of lumen 14 when ring 12 is in a relaxed condition. The two diametrically opposite files form a meshed array extending along the length of lumen 14 with alternate teeth 28 from opposite files successively obstructing the lumen in a single plane that axially bisects ring 12 and lumen 14. The embedded ends 30 of the clip elements 28 are shown as integral parts of anchor bars 32 completely embedded within and extending between opposite bases of ring 12, generally parallel to the axis of lumen 14. Several small holes 33 in the anchor bars 32 provide a greater band between adjoining surfaces of ring 12 and bar 32 by allowing the material of ring 12 to fill the holes as ring 12 is joined to clip 16 by such manufacturing techniques as extrusion or injection molding.

Figure 3A:
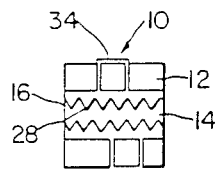
FIGS. 3A, 3B and 3C are a sectional front view, a side view, and a sectional frontview, respectively, of another embodiment.
Figure 3B:
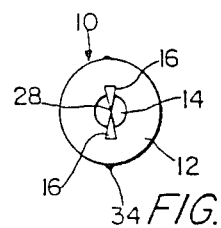
Figure 3C:
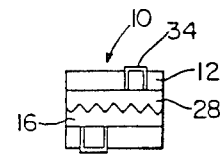

FIG. 3A shows a cross-section side view and FIG. 3B shows an end view of a ring clip device 10, suitable for occluding a linear organ structure, in a slightly stretched position. The ring clip is formed of a cylindrically shaped, stretchable solid, ring 12 having a centrally located lumen 14 extending between opposite bases. Ring 12 is made of non-tissue reactive materials having sufficient elasticity to perform the functions described herein. The teeth 28 of one or more serrated clips 16 (preferably a diametrically opposed pair of clips 16) are arranged in axially aligned files partially embedded within ring 12 to protrude into lumen 14. As shown in FIG. 3C, clips 16 are disposed diametrically opposite to each other so that when ring clip 10 resumes it unstretched state, the teeth mesh. Alternatively, clips 16 may be disposed slightly oblique to each other in two axial files and still mesh when the ring is in its relaxed state. Clips 16 are retentively held in place by anchors 34 while ring 12 is stretched and released. Preferably, clips 16 are made of government approved, non-tissue reactive materials (e.g., medical grades of plactic, Silastic, or stainless steel) that are relatively rigid in comparison to the materials of ring 12. When applied to a linear organ structure in the manner described herein, the organ is drawn into a loop extending through lumen 14. The occluding pressure of elastic ring 12 upon the organ, the interaction between teeth 28 and the occluded organ, and the meshed array formed around the occluded organ by teeth 28 as ring 12 resumes its relaxed condition combine to provide an effect which tends to resist movement or slippage of ring clip 10 along the organ.

Figure 4A:
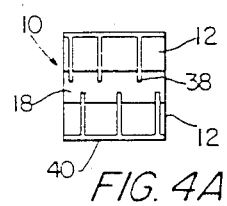
FIGS. 4A and 4B are a sectional front view and a side view, respectively, of another embodiment.
Figure 4B:
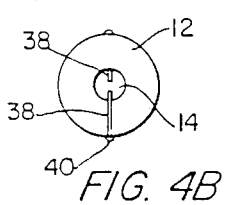
Figure 4C:
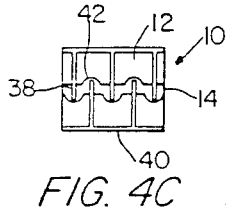
FIG. 4C is a sectional front view of another embodiment.

FIGS. 4A and 4B show a cross-sectional side view and an end view, respectively, of another ring clip ligating device 10 in a slightly stretched state. A plurality of diametrically opposed pins 38 are partially embedded in ring 12 so as to protrude into central lumen 14. When ring clip 10 is released, pins 38 form an interleaved array along the longitudinal axis of lumen 14. FIG. 4C shows a variation of the ring clip of FIG. 4A in a relaxed or unstretched state. The ring clip of FIG. 4C differs from that of FIG. 4A because one or more recesses 42 are regularly disposed into the interior surface of lumen 14 and embedded pins 38 are made slightly longer so as to not only protrude into lumen 14, but to extend across lumen 14 into interior recesses 42, thereby providing an interlocking action between ring 12 and the array of interleaved pins 38 when ring clip 10 is in its relaxed state. Additionally, ring clip 10 may be made with an anesthetic in a liquid, jelly or powdered form partially or completely filling recesses 42. When suddenly released from a stretched state, the rapid protrusion of the tips of pins 38 either dislodge the anesthetic from the recesses or penetrate a seal (not shown) covering the anesthetic within the recesses, thereby releasing the anesthetic to the surrounding environment of lumen 14. The seal could be a quick drying liquid coating applied to the inside of lumen 14 to cover recesses filled with an anesthetic. Alternatively, the seal could be applied to the inside of lumen 14 generally to cover recesses 42 and the protruding tips of pins 38 so that an initial stretching of ring 12 just prior to use will cause relative movement between the pins 38 and their associated recesses 42, thereby breaking the seal and releasing the anesthetic. If promptly used, enough of the anesthetic will remain within lumen 14 to provide an efficacious dosage at the site of the linear structure to which it is applied.

Figure 5A:
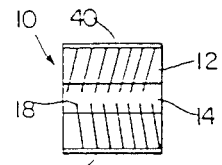
FIGS. 5A and 5B are a sectional front view and a side view, respectively, of another embodiment.
Figure 5B:
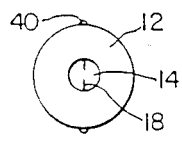

FIGS. 5A and 5B show a cross-section side views and an end view, respectively, of another embodiment of ring clip 10. One or more needles 18 slightly thinner in diameter than those pins shown in FIGS. 4A and 4B, are partially embedded within elastic ring 12 so as to protrude into or, alternatively extend completely across, lumen 14 with an oblique orientation when ring 12 is in a relaxed condition. Anchor rods 40 connecting the exterior tips of one or more meedles 18, and running along the sides of ring 12, either exterior to ring 12, as shown, or embedded within ring 12 somewhere between the interior wall of lumen 14 and the exterior sides of ring 12, may be used to prevent dislocation of needles while allowing lumen 14 to be freely expanded by stretching ring 12. When applied about a linear organ structure, the occluding pressure of elastic ring 12, the protrusion of needles 18 into or across lumen 14, and the interleaving of an array of needles 18 formed about the occluded organ as ring 12 resumes its relaxed condition, are complemented by the preferential orientation of needles 18 so as to resist movement of ring clip 10 along the organ.

Figure 6A:
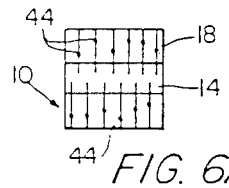
FIGS. 6A, 6B and 6C are a sectional front view, a side view, and a sectional front view, respectively, of another embodiment.
Figure 6B:
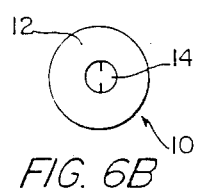
Figure 6C:
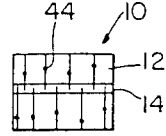

FIGS. 6A and 6B show a cross-section side view and an end view, respectively, of another embodiment of a ring clip 10. One or more needles 18 are arranged in axial alignment with an orientation perpendicular to lumen 14 and partially embedded in two diametrically opposite files within ring 12 with a straight orientation so as to form an interleaved array along the length of lumen 14 as shown in FIG. 6C, when elastic ring 12 is in its relaxed state. Discrete anchors 44, formed by enlarged segments of needles 18, serve to prevent dislocation of individual needles 20 while allowing ring 12 to be freely stretched.

Figure 7A:
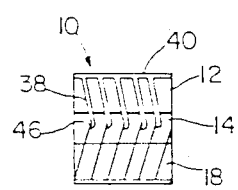
FIGS. 7A and 7B are a sectional front view and a side view, respectively, of another embodiment.
Figure 7B:
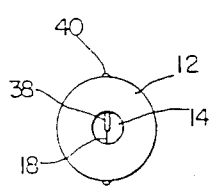

FIGS. 7A and 7B show a cross-section side view and an end view, respectively, of another embodiment of a ring clip 10 in a relaxed condition. One or more needles 18 partially embedded within ring 12 and protruding into lumen 14 in a single file along one side are arranged in alignment diametrically opposite a single file of partially embedded and protruding larger pins 38. The pins 38 may be made with grooves 46 at their distal ends so as to accommodate the protruding tips of individual pins 20 aligned in the opposite file when ring 12 is in its relaxed condition. Alternatively, grooves 46 may be dusted or filled with an anesthetic agent, or pins 38 made hollow and filled with an anesthetic agent, releasable by relative movement or physical interaction between the tips of needles 18 and grooves 46.

Figure 8:
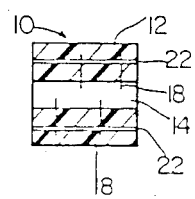
FIG. 8 is a sectional front view of another embodiment.

FIG. 8 shows a cut-away view of a relaxed ring clip 10 having two opposed files of needles 18 partially embedded with ring 12 and protruding into lumen 14. Anchor rods 22, either securely attached or integral with needles 18, are also embedded within ring 12 to prevent dislocation of needles 18 during stretching and relaxation of ring 12. In the configuration shown, ring 12 is in a relaxed condition. Needles 18 in each file merely obstruct lumen 14 and do not interact with those of the opposite file when ring 12 is in its relaxed condition.

Figure 9A:
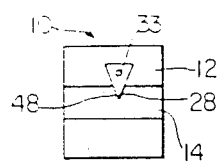
FIGS. 9A and 9B are a sectional front view and a side view, respectively of another embodiment.
Figure 9B:
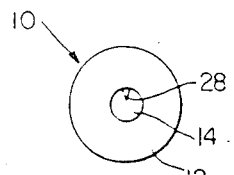

FIGS. 9A and 9B show a ring clip 10 having a single triangular tooth 28 partially embedded in ring 12 and protruding into lumen 14. A hole 33 in the embedded portion of tooth 28 allows the material of ring 12 to extend through, thus providing a more secure bond between ring 12 and clip member tooth 28. Both figures show that all sides of tooth 28 may be made to taper to a point. The sides of tooth 28 widens from its tip 48 so that at the point where tooth passes through the side of lumen 14 into ring 12, as well as along its embedded sides, tooth 28 presents sufficient surface area to the material of embedding ring 12 to prevent its dislocation due to tearing of the adjoining ring material during stretching and relaxation.

Figure 10A:
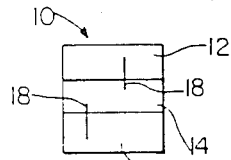
FIGS. 10A and 10B are a sectional front view and a side view, respectively, of another embodiment.
Figure 10B:
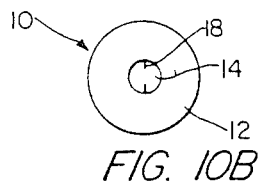

FIGS. 10A and 10B show a ring clip 10 having a pair of needle clips 18 partially embedded within ring 12 and protruding into the lumen from opposite sides.

Figure 11A:
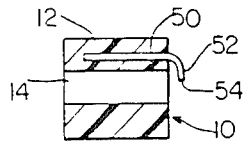
FIGS. 11A and 11B are a sectional front view and a side view, respectively, of another embodiment.
Figure 11B:
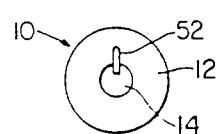

FIGS. 11A and 11B show a ring clip 10 containing a single, partially embedded clip element or rod 50. One end 52 of rod 50 protrudes from one end or base of ring 12 and is bent radially inward to partially cross and obstruct the orifice of lumen 14. The tip 54 of end 52 may be made blunt or sharp.

Figure 12A:
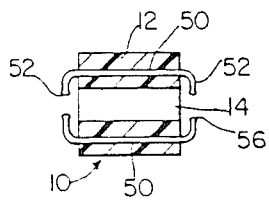
FIGS. 12A and 12B are a sectional front view and a side view, respectively, of another embodiment.
Figure 12B:
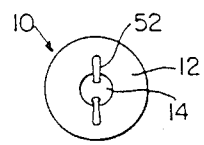

FIGS. 12A and 12B show a ring clip 10 containing a pair of parallel rods 50 partially embedded in opposite sides of ring 12. Both ends, 52 of rods 50 protrude from opposite bases of ring 12 and are bent radially inward to partially cross and obstruct opposite orifices of lumen 14. The ends 52 of opposite rods 50 nearly touch each other at their tips 56. Those tips 56 may be made round, either by crimping or fitting with a small ball to avoid tearing any anatomical tissue member.

Figure 13A:
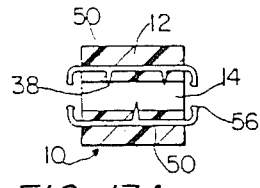
FIGS. 13A and 13B are a sectional front view and a side view, respectively, of another embodiment.
Figure 13B:
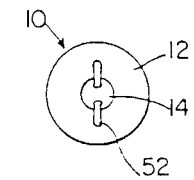

FIGS. 13A and 13B show a ring clip 10 containing a pair of barbed, parallel rods 50 partially embedded in opposite sides of ring 12. The barbs or pins 38 of rods 50 protrude into and partially obstruct lumen 14 while both ends 52 of rods 50 protrude from opposite bases of ring 12 and are bent radially inward to partially obstruct the orifices of lumen 14. The tips 56 of opposite rods 50 nearly touch, and may be made round.

Figure 14A:
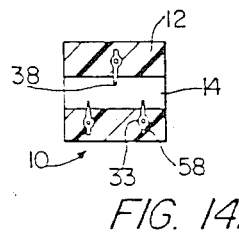
FIGS. 14A and 14B are a sectional front view and a side view, respectively, of another embodiment.
Figure 14B:
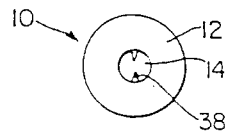

FIGS. 14A and 14B show a ring clip 10 with several pin type clip members 38 partially embedded in ring 12 and protruding into lumen 14 alternately from opposite sides. Each of the pins 38 has an enlarged embedded section 58 pierced by a hole 33. Both the enlarged section 58 and hole 33 serve to better anchor pins 38 within ring 12 during stretching and relaxation.

Figure 15A:
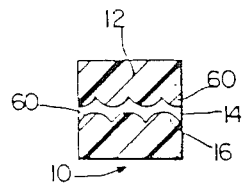
FIGS. 15A and 15B are a sectional front view and a side view, respectively, of another embodiment.
Figure 15B:
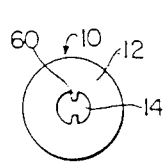
Figure 15C:
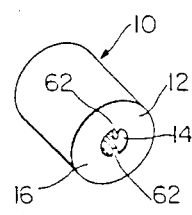

FIGS. 15A and 15B show a variation of a ring clip 10 in which clip 16 is formed of two diametrically opposite files of discrete axially aligned teeth 60 arranged so that teeth 60 in alternate interleaved files protrude into and partially obstruct lumen 14. These teeth 60 are integral extensions of ring 12. Teeth 60 may be made in several of various styles, for example, as relatively long and thin, protruding pins 18 or as short and wide knobs. Additionally, as shown in FIG. 15C, clip 16 may be made as two continuous diametrically opposite protrusions 62 of the same material as ring 12.

FIGS. 16A and 16B show another variation of a ring clip 10 in a relaxed condition. A clip 16 is formed by a hollow tube 64 longitudinally split by one or more divisions 66. Split clip 64 is surrounded by elastic ring 12. Clip teeth 68, shown as discrete, inwardly directed integral elements of split ring 64, form two opposite files in an interleaved array partially obstructing the coaxial lumen 14 of ring 12. Each file is joined to a split clip 64. Preferrably, the material of ring 12 has a higher modulus of elasticity than the material of split clips 64. During expansion of ring 12 by application of pressure against the interior walls of lumen 14, divisions 66 permits split clip 64 to move with the interior surface of lumen 14, thus providing a nearly unobstructed lumen which may be easily applied over the neck of a loop of a linear organ structure. After ring 12 is released to contract to its relaxed condition, split clips 64 also resumes their original orientation and the files of teeth resume their original diametric opposition, thereby firmly grasping any membrane (e.g., mesosalpinx) between the folds of the organ structure. When ring 12 is stretched so that lumen 14 is several times its relaxed diameter, opposite files of teeth are, in effect, retracted in opposition, leaving lumen 14 relatively unobstructed so that ring 12 may be easily placed over a looped tissue member.

Anchors 70 extending into ring 12 from the exterior circumferential surface of split clips 64, may be used to forstall axial dislocation between ring 12 and split clips 64. Each split clip 64 may have its own anchor or anchors.

Ring clip 10 is preferably made with a ring 12 of government-approved, non-tissue reactive materials having sufficient elasticity to perform the functions described herein, particularly the occlusion of a tissue member or organ after ring 12 is stretched and applied around a loop of the organ. Various rubbery materials may be used for ring 12. Examplary materials are silicone rubber such as that commercially available under the name of "Silastic", latex rubber or tetrafluoroethylene. Collagen or any other absorbable or non-absorbable elastic material not harmful to the organ tissue may also be used. The clips 16 embedded within rings 12, including needles 18, serrated teeth 28, pins 38, and their anchors 22, 32, 70, rods 50, and split clips 64 may be made of the same materials as ring 12. Preferably however, clips, their anchors, rods and split clips are made of medically approved materials having a lower moculus of elasticity and therefore, more rigidity, than the material of ring 12. Suitable materials are tetrafluoroethylene, plastics, synthetic resins, and stainless steel. Ideally, the materials of ring 12 and its associated or embedded clip 16 will be chosen to provide a strong bond between adjoining surfaces of the clip and the surrounding ring material, thereby alleviating the need for such restraining features as anchors 22, 32, 70.

The arrangement of ring clip 10 leads itself to mass production. Turning to FIG. 17, for example, the ring 12 may be extruded as a tube around a length of oppositely aligned, interleaved teeth 18 of clip 16 to provide a centrally located obstructed lumen 14 encompassing the tips or teeth of the clips. A length of the tube and its embedded clips may then be sliced across the width of the tube as indicated by sectional arrows 72, 72' to make several small occluding ring clips 10.

It is possible to use a ring clip 10 by simply stretching it and placing it over or around the neck of an anatomical linear organ structure while the tissue member is drawn into a loop. To protect a ligating band from impairment through loss of memory or even breakage due to undue stretching, however, it is desirable to use a ring loader to stretch the band and an applicator to retain the band in its stretched condition while placing it around a tissue member. FIG. 18 shows a ring loader 100, a ring dilator 130, and a ring applicator 200 of the types suitable for facilitating the use of a ligating band such as a ring clip 10. Ring loader 100 has a conic surface 102 with an elongated protrusion 104 extending from the apex 106 of conic surface 102. One or more longitudinal channels 108 extend from the tip of protrusion 104 to the base edge 110 of conic surface 102. The cross-sectional diameter of protrusion 104 may be made less than the relaxed diameter of the lumen 14 of a ring clip 10 so that the ring clip may be easily slipped onto the protrusion. As shown in FIG. 18A, a cross-sectional view of protrusion 104, the channels 108 are typically of the same dimensions and are preferably made diametrically opposite to each other in order to accept opposite files of clip teeth 18, 28, 38 in a relaxed elastic ring clip 10. Alternatively, if the clip teeth 18, 28, 38 are designed to mesh or extend more than halfway across the lumen 14 of a relaxed ring clip, it is preferable to use a ring loader with a protrusion 104 which is completely bisected by a ring clip accommodation channel 109 in order to assure that the tips or teeth of the ring clip are not bent or dislocated during the loading operation. FIG. 18C shows a cross-sectional view of a ring clip 10 with a relaxed elastic ring 12 at rest around a protrusion 104. The protruding teeth 38 are easily accommodated by channels 108 without contact between the teeth and ring loader 104.

Ring dilator 130 has four (or more) thin, flexible posts 132 joined in pairs which define and radiate from a central, deformable aperture 134. Opposite pairs of posts 132 are joined at their radially outward ends to form a pad 136 which may be comfortably pushed by a thumb or forefinger. In use, aperture 134 fits loosely around protrusion 104 and the sides of the aperture rest against the base 13 of ring clip 10. Ideally, the sides of aperture 134 completely cover the base 13 of ring clip 10 in order to uniformly distribute pressure over the surface of base 13. A person may use one thumb and one forefinger, or two thumbs or two fingers to press against pads 136. Posts 132 transmit the force applied by the fingers to the central aperture 134 which, in turn, pushes ring clip 10 along protrusion 104. After ring clip 10 passes over the apex 106 of loader 100, the increasing area of conic surface 102 reacts to the axial movement of the ring by applying a counter-pressure uniformly distributed over the interior surface of the ring clip's lumen. The counter-pressure causes the ring and its lumen to expand. With reference to FIG. 18D, it may be noted that as the ring clip expands, a greater length of its teeth 18, 28, 38 may be exposed, thus necessitating accommodation channels 108 with depth increasing in proportion to the cross-sectional diameter of the ring loader. The posts 132 of ring dilator are, in effect, articulated by the arcuate shape of their joining pads 136. This articulation permits posts 132 to rotate tangentially outward from aperture 134, thereby allowing aperture 134 to deform in order to continue to press against the base 13 of the ring clip while adapting to the increased cross-sectional diameter of conic surface 102.

The applicator 200 has a hollow intermediate cylinder B having a short distal segment longitudinally split by a pair of diametrically opposite clip teeth accommodation slots 228. Ring loader 100 has a cylindrical base surface 112 which fits snugly within the operating channel 208 defined by the bore of intermediate cylinder B. The base edge 110 mates smoothly with the distal edge 206 of the intermediate cylinder. The accommodation channels 108 at the base edge 110 conform in width and alignment to the clip teeth accommodation slots 228 of the intermediate cylinder. Aperture 134 of the ring dilator is thus able to push the ring clip 10 from the conic surface 102 of the loader and onto the exterior surface 202 of the intermediate cylinder without causing the pins, needles or teeth of the ring's clip element 16 to have deleterious contact with any portion of the ring loader. After one ring clip 10 is loaded unto the intermediate cylinder, ring dilator 130 is removed and another ring clip 10 is placed on protrusion 104 and the loading operation repeated until the desired number of ring clips are loaded onto the applicator. Alternatively, because the ring clips are quite small, two may be simultaneously loaded onto the intermediate cylinder via this procedure. After the rings are loaded onto the intermediate cylinder, ring loader is removed and the applicator is ready for use.

FIG. 18E shows the effect of an alignment between the accommodation channels 108 of the ring loader and the accommodation slots 228 of the intermediate cylinder B. If the tongs and nibs of the forcepts 224 are radially aligned with the accommodation slots 228, then the diametrically opposite protruding elements (18, 28, 38) of the ring's clip will also be radially aligned with the tongs and nibs.

FIG. 19 shows a ring loader 101 having an undulating conic surface 103. Preferably, the cross-sectional area of the conic surface 103 increases in either intermittant ramps or in continuous ramps of varying steepness.

FIG. 20 shows an alternative design for a derormable ring dilator 131. Two perpendicular pairs of parallel arms 133 are joined in alternate pairs at four arcuate pads 137 to form a cloverleaf pattern symmetrical about a central, deformable aperture 134. Outward tangential rotation of arms 133 allows central aperture 134 to expand to adapt to increasing cross-sectional area of the conic surfaces 102, 103 of ring loaders 100, 101.

FIGS. 21A and 21B show ring dilators that are suitable for pushing a ring clip unto the intermediate cylinder B of an applicator via ring loader 100, 101.

Turning now to FIG. 22, it may be seen that the applicators 200 prescribed for facilitating the use of a ring clip 10 are of the type having two or more telescoping cylinders A, B. The exterior surface 202 of a hollow intermediate cylinder B closely fits and is slidably movable along the interior surface of a shorter, hollow outer cylinder A. Preferably, the wall thickness 204 of the outer cylinder is equal to or greater than the wall thickness of a stretched elastic ring clip 10 and the wall thickness 206 of the intermediate cylinder B is about equal to the length of any clip teeth 18, 28, 38 protruding into lumen 14 of a stretched elastic ring clip. The bore of the intermediate cylinder B defines an operating channel 208 of sufficient cross-sectional area to accommodate a loop or fold 210 of a healthy linear or tubular organ structure 212 (i.e., at least a double thickness of a tissue member) and any intermediate membrane 214 (e.g., mesosalpinx). Grasping forceps 220 are slidably disposed within the operating channel 208 with the tongs and tips 224 of the forceps radially aligned with the longitudinal ring clip teeth accommodation slots 228 in the distal end of the intermediate cylinder B.

Operationally, the distal end of the intermediate cylinder B is extended so as to protrude beyond the distal end of the outer cylinder A and one or more elastic ring clips 10 are placed around the outer surface of the protruding distal end. The protruding clip teeth 18, 28, 38 of the ring clip are preferentially oriented to rest within the accommodation slots 228 of the intermediate cylinder. The applicator 220 is inserted through an opening or small incision into a body cavity of a patient and the forceps 220 extended from the operating channel and manipulated to grasp a bodily tissue organ 212. As the forceps 220 are retracted into the operating channel, they complete a firm grasp of the tissue member 212 and draw it into the operating channel 208, thereby forming the tissue member into a loop or fold with its vertex 218 firmly held between the closed tongs 224 of the grasping forceps. The forceps 220 may be retracted into the operating channel a sufficient distance to assure that the vertex 218 of the loop is beyond the proximal side of the outer or more distal of the ring clips loaded onto the B cylinder, thus assuring placement of a ring clip beyond the vertex or knuckle 218 of the grasped loop. Note that if the bore of the intermediate cylinder B is of insufficient diameter, or if the tissue member 212 is of unusual thickness, the distal end or base 206 of the intermediate cylinder will tend to abrade or even slice the sides of the loop, particularly if the wall thickness of the intermediate cylinder is so thin as to have a sharp end 206 at its base. Accordingly, the bore of the intermediate cylinder must be of sufficient size to receive a length of a loop of the desired organ structure.

Figure 24:
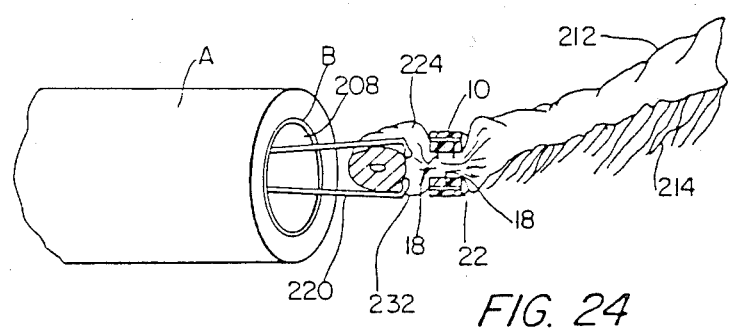
FIG. 24 is a partially cut-away isometric view showing another step in a method for using a ring clip.
Figure 25:
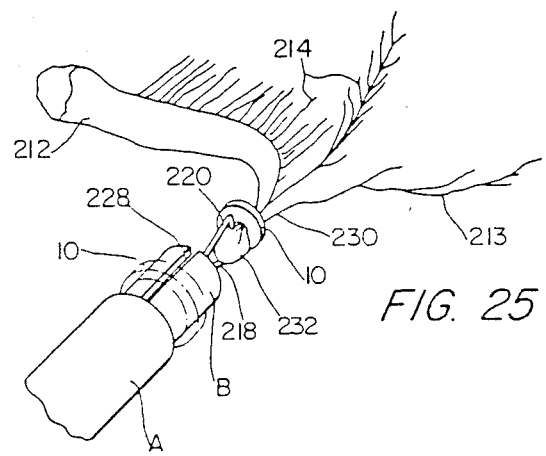
FIG. 25 is an orthogonal view showing another step in a method for using a ring clip.
Figure 26:
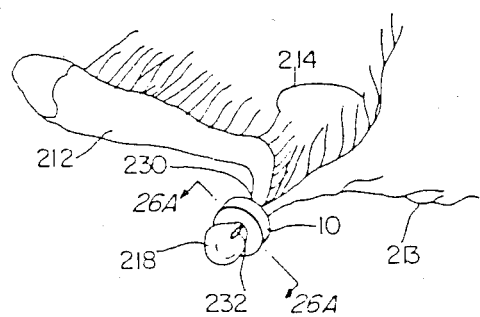
FIG. 26 is a front cross-sectional view showing a ring clip in use.
Figure 26A:
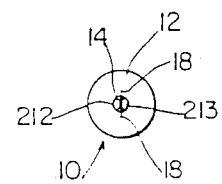
Figure 27:
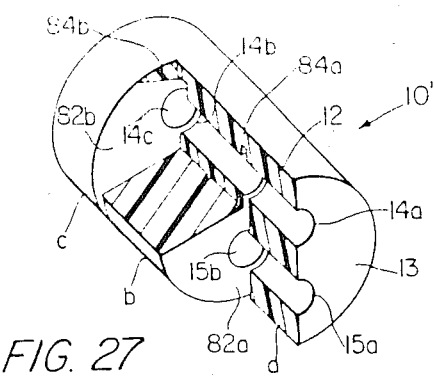
FIG. 27 is an orthogonal view of an alternative embodiment of a ring clip.

Turning now to FIG. 23, after retraction of the forceps, the intermediate cylinder is next retracted either partially or fully, with respect to the outer cylinder A, the radial edge of the shoulder formed by the distal base 204 of the outer cylinder A pushes one of the ring clips off the outer surface 202 of the intermediate cylinder B and over the neck 230 of the tissue member 212. As shown in FIGS. 24 and 25, the grasping forceps 220 are then again extended beyond the operating channel 208 sufficiently to release the vertex 218 of the tissue member 212 with the relaxed elastic ring clip 10 occluding the neck 230 of the looped or folded tissue member 212. Preferably, the ring clip 10 is placed close to the vertex 218 of the folded tissue member 212, just inside the inner bend of the loop 232 so as to limit the length of tissue member impaired by occlusion to as small a section as possible. Note that when the tongs and tips 224 of the forceps 220 grasp the vertex 218 of the tissue member, they circumferentially embrace the outside of the tissue member 212 so that the vertex 218 of the loop or fold of the tissue member 212 is completely within the tongs of the forceps 220 while the stretched ligating band 10 is pushed off the intermediate cylinder B and over the neck 220 of the fold. Consequently, as shown in FIGS. 26 and 27, any clip teeth 18 protruding into the lumen 14 of the ring clip 10 are oriented by the radial alignment of the tips 224 of forceps 220 and accommodation slots 228 to fit between the sides 212, 213 of the folded tissue member neck 210 because the tongs and tips 224 of the forceps 220 are radially aligned with the accommodation slots 228 of the intermediate cylinder B. This orientation of the clip teeth 18 assures that the teeth will physically obstruct the lumen 14 after application of ligating band 10. Thus, if there is any membrane or other tissue layer 214 such as a mesosalpinx adjoining the section of tissue member 210 grasped so that the edges of the loop of linear organ structure drawn into lumen 14 encompass the membrane 214, teeth 18 protrude through the loop between the organ structure and graspingly penetrate membrane 214, thereby preventing slippage of the ring clip 10 along the occluded tissue member 210 and over the vertex 218. The obstruction of the lumen 14 and the grasping penetration of membrane 214 is enhanced by the compression force of the elastic ring 12 upon the clips 16.

FIG. 27 shows in a partially cut-away view, another embodiment of a band for ligating a linear organ structure. The band 10', shown in a relaxed condition, is made of a segmented, solid ring 12 of an elastic material. The segmented ring 12 has a disc or cylindrical shape and contains a pair of parallel lumena 14, 15 extending between opposite bases 13. A clip action is provided by outer sections a and c of solid ring 12 coaxially disposed on either base 82a, 82b, respectively, of ring b. Sections a and c are flexibly hinged to ring b by solid intermediate sectors 84a, 84b. Preferably, sections a, c, ring b, and sectors 84a, 84b are all integral volumes of the same piece of segmented elastic material. In effect, each of sections a, c and ring b contain a pair of parallel lumena 14a, 15a, 14c, 15c, 14b, 15b, respectively. Each pair of lumena are diametrically aligned with sectors 84a, 84b. A straight line passing through the center of lumena 14, 15 bisets sectors 84a, 84b.

Figure 28:
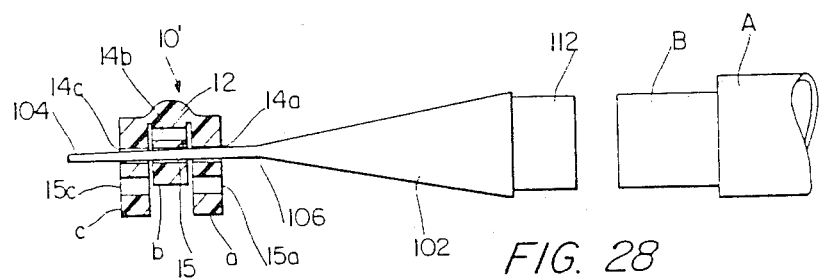
FIG. 28 is a partially cut-away front view shwoing a step in a method for use of a ring clip.

FIG. 28 shows one method of using ligating segmented ring clip 10'. During the operation for loading ring clip 10' onto the protrusion 104 of a ring loader, alternate lumena 14a, 15b and 14c are slipped unto the protrusion. The use of alternate lumena causes a displacement of ring b. Clip 12 is then stretched and loaded via conic surface 102 onto the intermediate cylinder B of an applicator. After clip 12 is slipped over the neck of a linear organ structure drawn into a loop by the applicator, the displacement of ring b relative to sections a and c creates a clip action by providing a strong lateral shearing force against the organ structure within the alternate lumena as sections a, c, and ring b return to their coaxial, relaxed condition.

Figure 29:
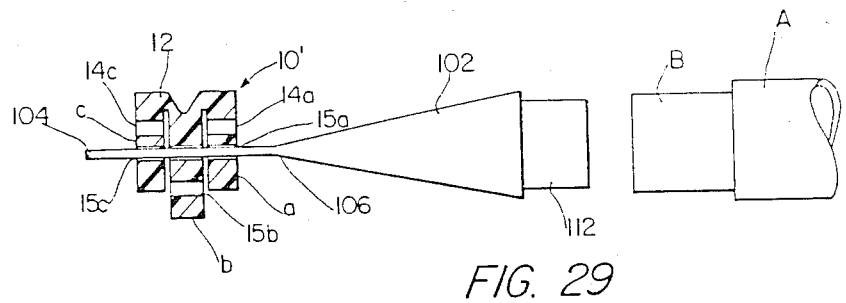
FIG. 29 is a partially cut-away view showing an alternate step in a method for use of a ring clip.

FIG. 29 shows an alternative method of using loading a segmented ring clip 12. In this method, alternate lumena 15a, 14b, 15c are loaded onto intermediate cylinder B of an applicator and then placed over the neck of a looped linear organ structure. The displacement of ring b relative to sections a and c also create a clip action by providing a lateral shearing force against the organ structure within the alternate lumena as sections a, c, and ring b return to their coaxial, relaxed condition. This force causes a sharp bend in the occluded structure which prevents segmented ring clip 12 from slipping along and over the neck of the loop.

Figure 30:
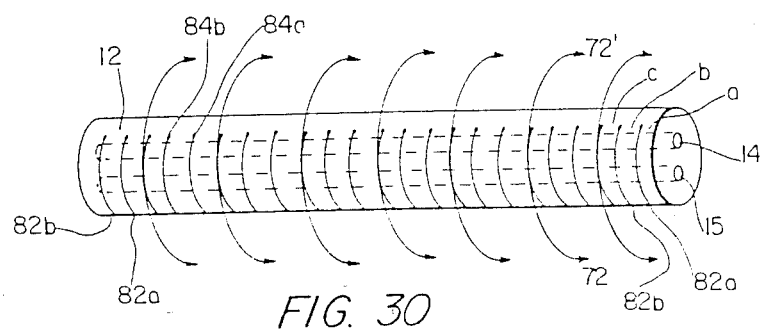
FIG. 30 is an isometric view showing one method for making the ring clip shown in FIG. 27.

FIG. 30 shows one method of making the segmented ring clip 12 of FIGS. 27, 28, and 29. Ring 12 may be extruded or molded as a solid rod of elastic material with a pair of parallel lumena 14, 15. Slices may then be made at section divisions 82a, 82b, almost severing sections a, c from ring b except for sectors 84a, 84b. Then, the rod may be sliced across its width as indicated by sectional arrows 72, 72' to provide several small segmented ring clips 12.

A particular advantage of the present invention is that after an anatomical linear or tubular organ structure is drawn into a knuckle and a ring clip 10 applied around the bend of the knuckle, the occluding force placed upon the organ by the ring clip 10 as elastic ring 12 relaxes causes the teeth 18, 28, 38 to protrude through the loop and at least one half of the way across the ring's lumen when the ring is in its relaxed state, thereby discouraging slippage of the ring over the knuckle. If there is a membrane such as a mesosalpinx attached to the organ, the membrane will occupy the central area of the knuckle intermediate to the loop and the teeth of the clip will penetrate the membrane, thereby firmly anchoring the ring in position and assuring that it will not slip over the knuckle. This advantage is particularly pronounced in a ring having two axial files of teeth extending radially toward the longitudinal axis of the lumen from diametrically opposite sides of the lumen to form an interleaved, interlocking or meshed array of teeth obstructing passage of the loop of the organ structure through the central passageway when the ring (and thus, the lumen) is in its relaxed state and, if a membrane is included within the knuckle, retentively grasping the membrane.

It is important to note that it is preferable for the clip elements (teeth or pins) to be arranged into one or two axial files of one or more teeth or pins on diametrically opposite sides of the lumen so that the clip elements are directed radially toward the center of the lumen to protrude through the loop or grasp the intermediate membrane rather than puncturing or otherwise piercing the two sides of the whatever linear or tubular organ structure forms the loop. Accordingly, the exposed ends of each of the clip elements should equal at least one-fourth (i.e., the exposed length of each clip element should at least equal one-eighth of the lumen diameter so that together diametrically opposite files of teeth extend across at least one-fourth of the lumen diameter when the ring is in its relaxed state) and preferably one-half or more of the distance between the interior lumen surface and the longitudinal axis of the lumen 14 when the ring is in is relaxed state. Ideally, the exposed clip element distal sections each extend across one-half or more of the diameter of the lumen when the ring is in its relaxed state. When a ring clip is first released around the neck of a loop, the ring can not immediately assume its relaxed state because the bulk of the loop and any intermediate tissue completely fills the volume of lumen 14. Consequently, if the exposed ends of the clip elements are of insufficient length, they will not protrude signifucantly into the loop until after the ring has remained on the loop long enough to assume a more relaxed state due to a diminution of the bulk of the loop.

Another particular advantage of the ring clip is that its retentive clip feature allows it to be placed just inside the very tip of the knuckle with assurance that it will not slip over the knuckle before fibrosis of the ring occurs. This means that much shorter length of tissue organ is subjected to damage, thereby permitting recanalization of the ends adjacent the occluded segment of a linear organ structure such as a Fallopian tube in a subsequent surgical procedure.

It should be noted that FIGS. 1 through 30 are diagrammatic in nature and the dimensions of the various elements are shown as merely illustrative of the various possible features of the described invention. It is therefore, apparent that examination of these drawings will show that one or more of the dimensions of the various features illustrated are exaggerated with respect to other dimensions in order to more clearly show the relation of such features with other elements of an embodiment.

The term "elastic" is used to indicate the propensity of an object for recovering its size and shape after deformation by forces such as stretching.

It should also be noted that the ring clip disclosed, if of the proper size and occluding power, may be applied to ligate any one of several anatomical tissue members, whether a tubular linear organ structure such as a reproductive tubular member (e.g., Fallopian tube or vas deferens) or a vascular tubular structure such as an artery or vein, or whether a linear organ structure such as a ligament. The ring clip may be used for shortening linear organ structures as well as for occluding tubular organ structures.

I claim:

1. A band for surgically ligating an anatomical organ structure, comprising:
   a first, second and third ring of an elastic material serially connected by peripheral sectors and each having first and second discrete and axially aligned expansible lumina with centers radially aligned with said peripheral sectors.

2. The band of claim 1, wherein one of said first, second and third rings may be axially displaced relative to the other ones of said rings to provide axial alignment between the first lumina of said one of said rings and the second lumina of said other ones of said rings.

3. The band of claim 1, wherein said rings are annular and in parallel planes and said sectors are integral with and symmetrically positioned between said rings adjacent their outer circumferences.

4. The band of claim 3, wherein said rings are coincident to include the sectors while in a rest position.

5. The band of claim 1, wherein the axes of the first and second lumina are congruent in a rest position.

6. The band of claim 1, wherein said rings are substantially annular and lay in parallel planes in a rest position, and said sectors are integral with the outer edges of the rings.

7. The band of claim 1, wherein said rings and said sectors are an integral volume of the same piece of segmented elastic material with said rings lying in parallel planes and said sectors disposed between said rings adjacent their outer circumferences.

8. A ligating device, comprising:
   first, second and third masses of elastic material, each of said first, second and third masses providing discrete expansible first and second lumina; and
   a plurality of interconnecting elements made of said elastic material joining said first, second and third masses together in a serial array with said first lumina in said first, second and third masses being axially aligned;
   whereby one of said masses may be laterally displaced relative to the other ones of said masses and substantially within a plane transverse to an axis of a first one of said lumina in said one of said masses to provide axial alignment between said first one of said lumina in said one of said masses and the second ones of said lumina in said other ones of said masses.

9. The device of claim 8, further comprised of said plurality of interconnecting elements joining said masses together in an array with said first and second lumina in said first, second and third masses being axially aligned when said elastic material is in a relaxed state.

10. The device of claim 9, further comprised of said first and second lumina being diametrically aligned with said plurality of interconnecting elements.

11. The device of claim 8, further comprised of:
    said plurality of interconnecting elements joining said masses together in said array with said first and second lumina in said first, second and third masses being axially aligned when said elastic material is in a relaxed state; and said first and second lumina being diametrically aligned with said plurality of interconnecting elements.

12. The device of claim 8, wherein said masses are annular and lie in parallel planes, and said interconnecting elements are integral with and symmetrically positioned adjacent the outer circumferences of all of said masses.

13. The device of claim 8, wherein said masses and their lumina are congruent when said elastic material is in a relaxed state.

14. The device of claim 8, wherein said masses are substantially annular and lie in parallel planes when said elastic material is in a relaxed condition, and said interconnecting elements are integral with the outer edges of the masses.

15. The device of claim 11, wherein said masses are annular and lie in parallel planes, and said interconnecting elements are integral with an symmetrically positioned adjacent the outer circumferences of all of said masses.

16. The device of claim 11, wherein said masses and their lumina are congruent when said elastic material is in a relaxed state.

17. The device of claim 11, wherein said masses are substantially annular and lay in parallel planes when said elastic material is in a relaxed condition, and said interconnecting elements are integral with the outer edges of the masses.

18. A band for surgically ligating an anatomical organ structure, comprising:
   three substantially solid like bodies, each having first and second discrete expansible apertures, each body being composed of elastic material, the bodies having a mutually relative operative position and a rest position; and
   integral, elastic means disposed between pairs of said bodies for interconnecting the bodies in a serial array with a central one of said bodies being disposed between the other ones of said bodies and said apertures being substantially axially aligned in the rest position, wherein said central one of said bodies may be laterally displaced relative to the other ones of said bodies substantially within a plane transverse to an axis of one of the apertures from said rest position to the operative position with the first ones of said apertures in said other ones of said bodies being axially aligned with the second one of said apertures in said central one of said bodies, for urging the bodies in the operative position back toward the rest position.

19. The band of claim 18, further comprised of said elastic means joining said like bodies together in a serial array with said first and said second apertures in each of said like bodies being axially aligned when said elastic material is in a relaxed state.

20. The band of claim 19, further comprised of said first and second apertures being diametrically aligned with said elastic means.

21. The band of claim 18, further comprised of:
   said elastic means joining said like bodies together in said serial array with said first and second apertures in each of said like bodies being axially aligned while said elastic material is in a relaxed state; and
   said first and second apertures being diametrically aligned with said elastic means.

22. A band for surgically ligating an anatomical organ structure, comprising:
   first, second and third rings of an elastic material, each of said rings being axially perforated by first and second expansible lumina, said rings being serially ordered with said second ring being disposed between said first and third rings while said rings are in a rest position, axes of said first lumina being aligned while said rings are in the rest position and axes of said second lumina being aligned while said rings are in the rest position,
   said second ring having a pair of opposite major exterior surfaces disposed facing and substantially parallel to like major exterior surfaces of said first and third rings, facing major exterior surfaces of said first and second rings being separated everywhere but along a first sector adjoining peripheries of said facing major exterior surface of said first and second rings, facing major exterior surfaces of said second and third rings being separated everywhere but along a second sector adjoining peripheries of said facing major exterior surfaces of said second and third rings, and
   said first and second sectors being axially aligned while said rings are in the rest position whereby said second ring may be radially disposed relative to said first and third rings to provide alignment of the axes of said first lumina of said second ring with axes of said second lumina of said first and third rings.

23. The device of claim 22, wherein the axes of the first and second lumina are congruent in a rest position.

24. The band of claim 22, wherein said rings are substantially annular and lay in parallel planes in a rest position, and said sectors are integral with the outer edges of the rings.

25. The band of claim 22, wherein said rings and said sectors are an integral volume of the same piece of segmented elastic material with said rings lying in parallel planes and said sectors disposed between said rings adjacent their outer circumferences.

26. The device of claim 22, further comprised of said first and second sectors joining said masses together in an array with said first and second lumina in said first, second and third rings being axially aligned when said elastic material is in a relaxed state.

27. The device of claim 26, further comprised of said first and second lumina in each of said first, second and third rings being diametrically aligned with said first and third sectors.

* * * * *